United States Patent [19]

Spector

[11] Patent Number: 4,696,844

[45] Date of Patent: Sep. 29, 1987

[54] FILM TYPE AIR FRESHENER

[76] Inventor: Donald Spector, 380 Mountain Rd., Union City, N.J. 07087

[21] Appl. No.: 932,610

[22] Filed: Nov. 20, 1986

[51] Int. Cl.⁴ ............................ B32B 3/14; B44C 1/28
[52] U.S. Cl. ........................................ 428/46; 428/49; 428/905
[58] Field of Search ..................... 428/905, 13, 46, 48, 428/49; 239/34, 54

[56] References Cited

U.S. PATENT DOCUMENTS

| | | | |
|---|---|---|---|
| 2,169,055 | 8/1939 | Overshiner | 106/180 X |
| 2,577,320 | 12/1951 | Fenyo | 428/905 X |
| 3,216,882 | 11/1965 | Feldt et al. | 428/131 |
| 3,578,545 | 5/1971 | Carson et al. | 428/905 X |
| 3,655,129 | 4/1972 | Selner | 239/34 X |
| 3,685,734 | 8/1972 | Paciorek et al. | 428/401 X |
| 3,994,439 | 11/1976 | Van Breen et al. | 239/54 |
| 4,051,159 | 9/1977 | Tsoucalas et al. | 239/34 X |
| 4,077,926 | 3/1978 | Sanderson et al. | 526/312 X |
| 4,277,024 | 7/1981 | Spector | 428/905 X |
| 4,283,011 | 8/1981 | Spector | 428/79 X |
| 4,418,099 | 11/1983 | Cuevas et al. | 427/229 |
| 4,419,396 | 12/1983 | Sugimoto | 428/905 X |
| 4,493,869 | 1/1985 | Sweeny et al. | 428/905 X |
| 4,547,122 | 10/1985 | Leech | 428/49 X |
| 4,555,438 | 11/1985 | Orsak et al. | 428/905 X |

Primary Examiner—Henry F. Epstein
Attorney, Agent, or Firm—Michael Ebert

[57] ABSTRACT

A replaceable air freshener primarily for use on the tiled wall of a bathroom or kitchen. The air freshener is formed by a transparent plastic film of polymeric material whose dimensions match those of a standard tile, the rear face of the film having a low tack, clear adhesive thereon whereby the film may be laminated to a selected tile on the wall or readily removed therefrom. The film is constituted by a polymeric matrix having myriad cells dispersed therein impregnated with a volatile fragrance which is slowly released from the film into the atmosphere of the room. Screened on the front face of the film is an artwork having a background field imparted thereto by the color of the tile onto which the film is laminated so that the artwork is then in harmony with the tiled wall. The emitted fragrance is thematically related to the artwork so that should the artwork be an Xmas tree, the fragrance will be that of pine.

6 Claims, 3 Drawing Figures

FILM TYPE AIR FRESHENER

BACKGROUND OF INVENTION

1. Field of Invention:

This invention relates generally to air fresheners which release an aroma into the atmosphere of a room, and more particularly to a replaceable air freshener in the form of a film which is adhered to a wall tile and which emits an aroma that is thematically related to an artwork screened on the film.

2. Status of Prior Art:

As used herein, the term "aroma" or "fragrance" is not limited to perfume-like odors, but encompasses any odor that is suitable as an air freshener to condition, modify or otherwise charge the ambient atmosphere.

The aroma of perfumes and perfume-based products such as colognes and toilet waters was originally derived from the essential oil of plants. However, since the early 19th century, chemists have succeeded in analyzing many essential oils and in creating thousands of synthetics, some simulating natural products and others yielding altogether new scents. Perfumes today are largely blends of natural and synthetic scents and of fixatives which equalize vaporization and enhance pungency. In most liquid scents, the ingredients are combined with a highly volatile alcohol carrier.

The environment of a kitchen or bathroom may be rendered unpleasant by food and cooking smells as well as toilet and other pungent odors. The common practice, therefore is to mask or modify the prevailing atmosphere by some sort of air freshener.

It is known to provide an air freshener or fragrance generator in the form of a bottle containing a volatile liquid in which a wick is immersed, the upper end of the wick extending above the bottle and being exposed to the air. Such devices are subject to spillage or leakage; and in order to adjust the rate of volatilization, means must be provided to vary the extent of wick exposure.

The typical commercial air freshener has a strictly utilitarian appearance which clashes with many household decors. It is for this reason that a commercial air freshener is often placed where it is out of sight. On the other hand, an air freshener is most effective when placed in an exposed open area where it is subjected to maximum air flow. By hiding the air freshener in a confined area, one thereby renders it less effective for its intended function, which is to permeate the prevailing atmosphere with a pleasing fragrance.

The present invention provides an air freshener which by its very nature is located at an open area where it is exposed to a free flow of air, the freshener making use of a film of polymeric material impregnated with a volatile fragrance. The concept of gradually releasing a volatile fragrance over an extended period of time from a plastic film is well known and is disclosed, for example, in U.S. Pat. No. 2,169,055. In this patent, a fragrance emitting film is produced by mixing essential oils and a solvent therefor into a cellulose acetate solution from which films are formed, the solvent for the oils being quickly evaporated, after which the essential oils slowly volatilize.

Various other forms of controlled fragrance films are disclosed in the following patents:

U.S. Pat. No. 4,419,396
U.S. Pat. No. 4,051,159
U.S. Pat. No. 3,994,439
U.S. Pat. No. 3,685,734
U.S. Pat. No. 3,655,129

SUMMARY OF INVENTION

The primary object of this invention is to provide an air freshener which also is a work of art and therefore can be conspicuously placed at an open site that is conducive to the most effective operation of the air freshener, the fragrance emanating from the air freshener being thematically related to the artwork displayed thereby so that a viewer's visual impression thereof is accompanied by an olfactory impression which enhances the enjoyment of the work.

More particularly, an object of the invention is to provide an air freshener of the above type in which the artwork is screened onto the front face of a transparent, fragrance-emitting polymeric film which is adherable onto any smooth surface, such as one a glazed tile, whereby the freshener is then exposed to ambient air movement that promotes its efficient operation.

A significant feature of the invention is that when the air freshener film is laminated to a ceramic tile whose glazed face has a solid color, effectively imparted as a background field to the artwork screened on the film is the solid color; hence the laminated tile is in harmony with unlaminated tiles in an array thereof on the wall and the artwork merges with the tiled wall and does not introduce a discontinuity therein.

Also an object of the invention is to provide air fresheners each having a different artwork thereon which lend themselves to selective grouping on the part of a user who can express his own taste by creating a multiple air freshener having a composite fragrance or bouquet.

Briefly stated, these objects are attained in a replaceable air freshener primarily for use on the tiled wall of a bathroom or kitchen. The air freshener is formed by a transparent plastic film of polymeric material whose dimensions match those of a standard tile, the rear face of the film having a low tack, clear adhesive thereon whereby the film may be laminated to a selected tile on the wall or readily removed therefrom. The film is constituted by a polymeric matrix having myriad cells dispersed therein impregnated with a volatile fragrance which is slowly released from the film into the atmosphere of the room. Screened on the front face of the film is an artwork having a background field imparted thereto by the color of the tile onto which the film is laminated so that the artwork is then in harmony with the tiled wall. The emitted fragrance is thematically related to the artwork so that should the artwork be an Xmas tree, the fragrance will be that of pine.

BRIEF DESCRIPTION OF DRAWINGS

For a better understanding of the invention as well as other objects and further features thereof, reference is made to the following detailed description to be read in conjunction with the accompanying drawings, wherein.

DESCRIPTION OF INVENTION

Figure 1:
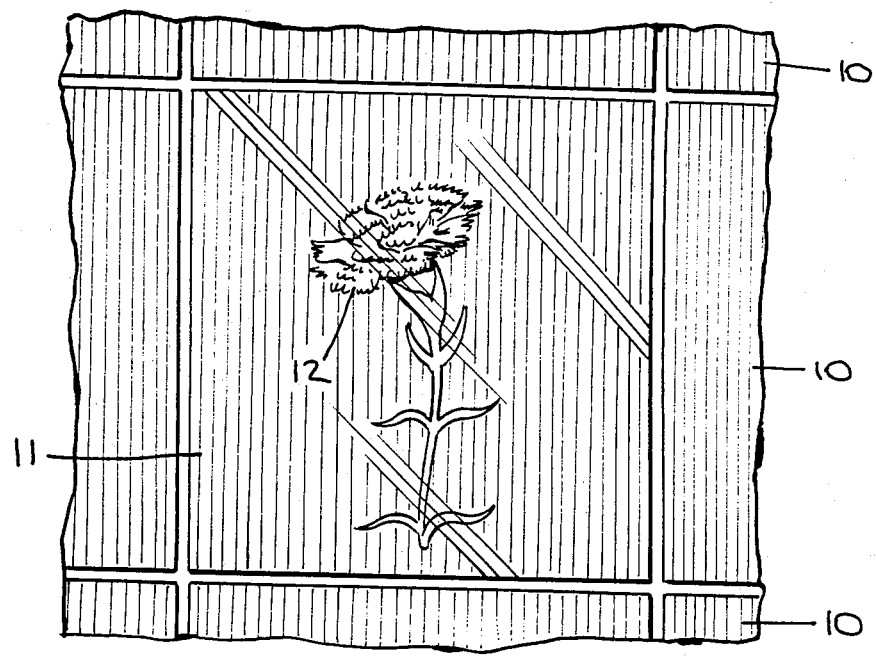
FIG. 1 shows an air freshener film square in accordance with the invention.
Figure 2:
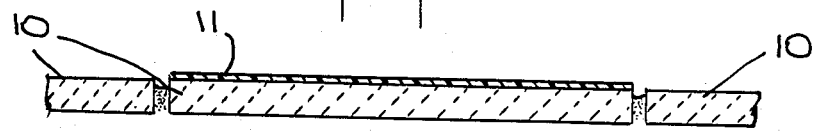
FIG. 2 is a section taken through a ceramic tile having the air freshener laminated thereto.

Referring now to FIGS. 1 and 2, there is shown a tiled wall composed of an array of ceramic or composition tiles 10 having a smooth or glazed surface. This surface has a solid color, such as white, blue, green, etc. Such tiled walls are typically found in bathrooms, kitchens and in other environments where the need exists for an air freshener to render the atmosphere more pleasing.

Adhered to any one of tiles 10 is an air freshener 11 which takes the form of a flexible, transparent, rectangular or square film 11 impregnated with a volatile fragrance in a relatively high concentration, preferably 20 to 30%. The dimensions of the film match those of tile 10; hence when adhered to the tile, the color of the tile is seen through the film and a viewer is not aware of the presence of the film.

The fragrance-emitting film may be of any known type and is preferably made of a bi-axially oriented polymeric material so that it is non-stretchable in either direction. The film thickness, which may be of about three to six mils, determines the fragrance-emitting capacity of the air freshener. In practice, the film is protectively covered on both faces thereof with release sheets which are peeled off only before the film is laminated to the file so that no loss of fragrance is experienced during storage.

The rear face of film 11 is coated with a clear, low-tack, pressure-sensitive adhesive such as that used by 3M on its "Post-Em" sheets. Hence the film can be easily removed from the tile when its fragrance is exhausted after a few weeks and replaced by a fresh film.

Screened or otherwise imprinted on the front face of film 11 is a work of art 12 which in the example shown is a carnation flower. The fragrance impregnated in film 11 in this instance is a carnation fragrance so that the viewer not only sees a carnation but at the same time smells this flower. It is not essential to the invention that there be a match between the artwork and the fragrance, but only that the two be thematically related.

Thus, should the artwork be that of an ocean-going luxury liner, the fragrance may be that of a sea breeze; and should the artwork be that of wood burning in a fireplace, the thematically related fragrance may be a fragrant mixture suggesting a fireplace. Or in the case of an artwork showing a basket of different fruits, the aroma can be that of a bouquet of fruit fragrances.

In practice, the artwork may be a reproduction of a known masterpiece, such as Monet's classic painting of water lillies, in which case the fragrance would be that of lillies. The world of art is replete with paintings of organic objects such as flowers, trees, vegetables, etc., which have characteristic odors, and by screening these works on the films emitting thematically related fragrances, one then provides an air freshener which not only renders the ambient air more pleasing but also affords the occupant of the room with a work of art whose visual impression is enhanced by a thematically-related olfactory impression.

Figure 3:
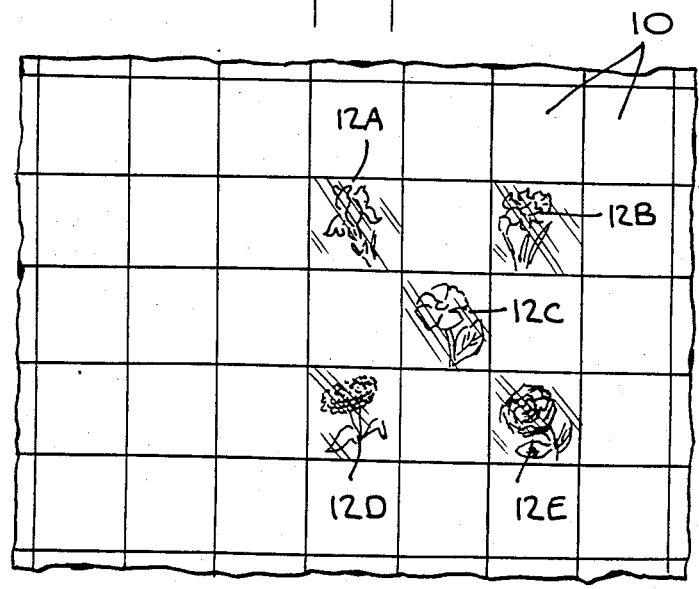
FIG. 3 shows a tiled wall on which is applied a pattern of air fresheners.

The air freshener in accordance with the invention lends itself to creative selective grouping on the part of the user. Thus, as shown in FIG. 3, one may apply to selected tiles 10 in any array of tiles on a tiled wall, a geometric pattern of five air fresheners having different artworks 12A to 12E therein. Each work can, for example, represent a different flower, and each film will then emit an aroma related to the flower screened thereon. In this way, the user is able to create a bouquet of flowers and a corresponding bouquet of aromas.

It is important to note that the artwork on the transparent film is imposed on a field which is the color of the underlying tile. Thus, if the tile color is green and the work of art is a rose flower, the flower is seen against a green field. Since the tiled wall is green and the laminated tile is also seen as green since the film is transparent, the laminated tile does not introduce a discordant note in the wall, and the work of art appears to be imposed on the wall, not on a blank space in the wall.

The film may, in practice, be applied to surfaces other than tiles. Thus, one may place the film on the window of an automobile, and thereby render the interior atmosphere thereof more pleasing. The fragrance emitted in this instance may be a stimulant to discourage the driver from falling asleep at the wheel. Or one can laminate the film to the corner of the glass window-door of a bathroom cabinet.

While there has been shown and described a preferred embodiment of a film type air freshener in accordance with the invention, it will be appreciated that many changes and modifications may be made therein without, however, departing from the essential spirit thereof. Thus, the ink used to print the artwork on the film may incorporate therein a volatile fragrance whose aroma is thematically related to the artwork, so that this fragrance is exuded from the artwork for a prolonged period.

I claim:

1. An air freshener in combination with a wall tile having predetermined dimensions and a smooth surface having a solid color, which tile is identical to other tiles in an array thereof on the same wall, comprising:

A a transparent, flexible film of polymeric material having substantially the same dimensions as the tile impregnated with a volatile fragrance that is slowly released from the film, the fragrance being in a concentration resulting in a relatively prolonged emission thereof from the film;

B a low-tack, pressure-sensitive adhesive coating on the rear face of the film whereby the film may be adhered onto said tile and later peeled therefrom without difficulty when the fragrance is exhausted; and C an artwork imprinted on the film, the fragrance being thematically related to the artwork, whereby the visual impression made by the artwork is enhanced by the fragrance and the artwork is seen against the color of the tile which is the same as the other wall tiles.

2. An air freshener as set forth in claim 1, wherein said film has a thickness in the range of about three to six mils.

3. An air freshener as set forth in claim 1, wherein the film is bi-axially oriented.

4. An air freshener as set forth in claim 1, wherein said artwork has a floral subject matter, and the fragrance is a floral aroma.

5. The combination as set forth in claim 1, wherein said tile is a ceramic tile having a glazed surface.

6. The combination as set forth in claim 1, wherein said artwork imprinted on the film is printed thereon with an ink that incorporates a volatile fragrance that is exuded from the artwork for a prolonged period.

* * * * *